United States Patent
Lidman et al.

(10) Patent No.: US 6,937,902 B2
(45) Date of Patent: Aug. 30, 2005

(54) PACEMAKER WITH DETERMINATION OF THE DEPENDENCY OF CARDIAC OUTPUT ON THE AV-DELAY

(75) Inventors: Johan Lidman, Stockholm (SE); Nils Holmström, Järfälla (SE); Kjell Norén, Solna (SE)

(73) Assignee: St. Jude Medical AB, Järfälla (SE)

( * ) Notice: Subject to any disclaimer, the term of this patent is extended or adjusted under 35 U.S.C. 154(b) by 290 days.

(21) Appl. No.: 10/258,645

(22) PCT Filed: Apr. 23, 2001

(86) PCT No.: PCT/SE01/00875

§ 371 (c)(1),
(2), (4) Date: Oct. 25, 2002

(87) PCT Pub. No.: WO01/80947

PCT Pub. Date: Nov. 1, 2001

(65) Prior Publication Data

US 2003/0055462 A1 Mar. 20, 2003

(30) Foreign Application Priority Data

Apr. 27, 2000 (SE) ................................................ 0001534

(51) Int. Cl.$^7$ ............................................... A61N 1/365
(52) U.S. Cl. ............................. 607/27; 607/23; 607/9; 607/22; 600/526; 600/513
(58) Field of Search ............................... 607/9, 17, 22, 607/23, 24, 27; 600/513, 526

(56) References Cited

U.S. PATENT DOCUMENTS

| 5,024,222 | A | | 6/1991 | Thacker |
| 5,330,511 | A | * | 7/1994 | Boute ........................... 607/25 |
| 5,334,222 | A | * | 8/1994 | Salo et al. ...................... 607/17 |
| 5,441,522 | A | * | 8/1995 | Schuller ........................ 607/9 |
| 5,487,752 | A | | 1/1996 | Salo et al. |
| 5,540,727 | A | | 7/1996 | Tockman |
| 5,643,327 | A | | 7/1997 | Dawson et al. |
| 5,814,077 | A | * | 9/1998 | Sholder et al. ................ 607/9 |
| 5,891,176 | A | | 4/1999 | Bornzin |

\* cited by examiner

Primary Examiner—Kennedy Schaetzle
(74) Attorney, Agent, or Firm—Schiff Hardin LLP (57) ABSTRACT

A cardiac pacemaker has a pulse generator for delivering stimulation pulses to a patient's heart and a control unit for controlling the delivery of the stimulation pulses from the pulse generator. The control unit includes an altering unit for altering the AV-delay value from a predetermined first AV-delay value to a predetermined second AV-delay value, and back to the first AV-delay value. A sensor measures a parameter related to cardiac output of the patient, the sensor measuring this parameter in a time window within a time of operation with the first AV-delay value, and in a time window within the time of operation with said second AV-delay value, and in a time window within the time of operation after the return back to the first AV-delay value. A calculation unit calculates respective average values of the parameter during each of the time windows, and a determining unit determines from these average values which of the AV-delay values results in a higher cardiac output.

18 Claims, 6 Drawing Sheets

PACEMAKER WITH DETERMINATION OF THE DEPENDENCY OF CARDIAC OUTPUT ON THE AV-DELAY

BACKGROUND OF THE INVENTION

1. Field of the Invention

The present invention relates to a pacemaker of the type having a pulse generator for delivering stimulation pulses to a patient's hear and a control unit for controlling the delivery of stimulation pulses from the pulse generator, the control unit having an altering unit for altering the AV-delay from a predetermined first AV-delay value to a predetermined second AV-delay value, and back to the first AV-delay value, and a sensor being provided to measure a parameter related to cardiac output of the patient.

2. Description of the Prior Art

The PV-interval between the occurrence of an intrinsic P-wave and the application of a cardiac stimulation pulse can be different from the AV-interval between consecutive cardiac stimulation pulses to the atrium and the ventricle.

The term AV delay means the interval between the occurrence of a paced or an intrinsic P-wave and the application of a cardiac stimulation pulse to the ventricle of the heart.

It is well known that cardiac output of a human being is dependent on the 20 AV-delay, see e.g. U.S. Pat. Nos. 5,024,222, and 5,487,752, and 5,540,727, and 5,643,327 and 5,891,176. In all these patents, techniques are described for studying the variation of a cardiac performance parameter of the heart as a function of ao AV-delay in order to optimize the cardiac output. Thus U.S. Pat. No. 5,487,752 discloses a cardiac stimulator system including means for monitoring and pacing two chambers of the heart with pulses providing predetermined AV intervals. One of the AV intervals represents a base line value and the system is operated with this AV interval for a relatively long time, e.g. during 20 beats. The AV interval is changed for relatively few beats, e.g. 5 beats, and is then allowed to return to the base line value. A cardiac performance parameter is measured during these times of different AV intervals and from these measurements it is determined whether an improvement in said cardiac performance parameter over the base line value occurs when the AV interval is changed. By performing this procedure for different AV intervals an optimum AV interval can be determined.

Figure 1:
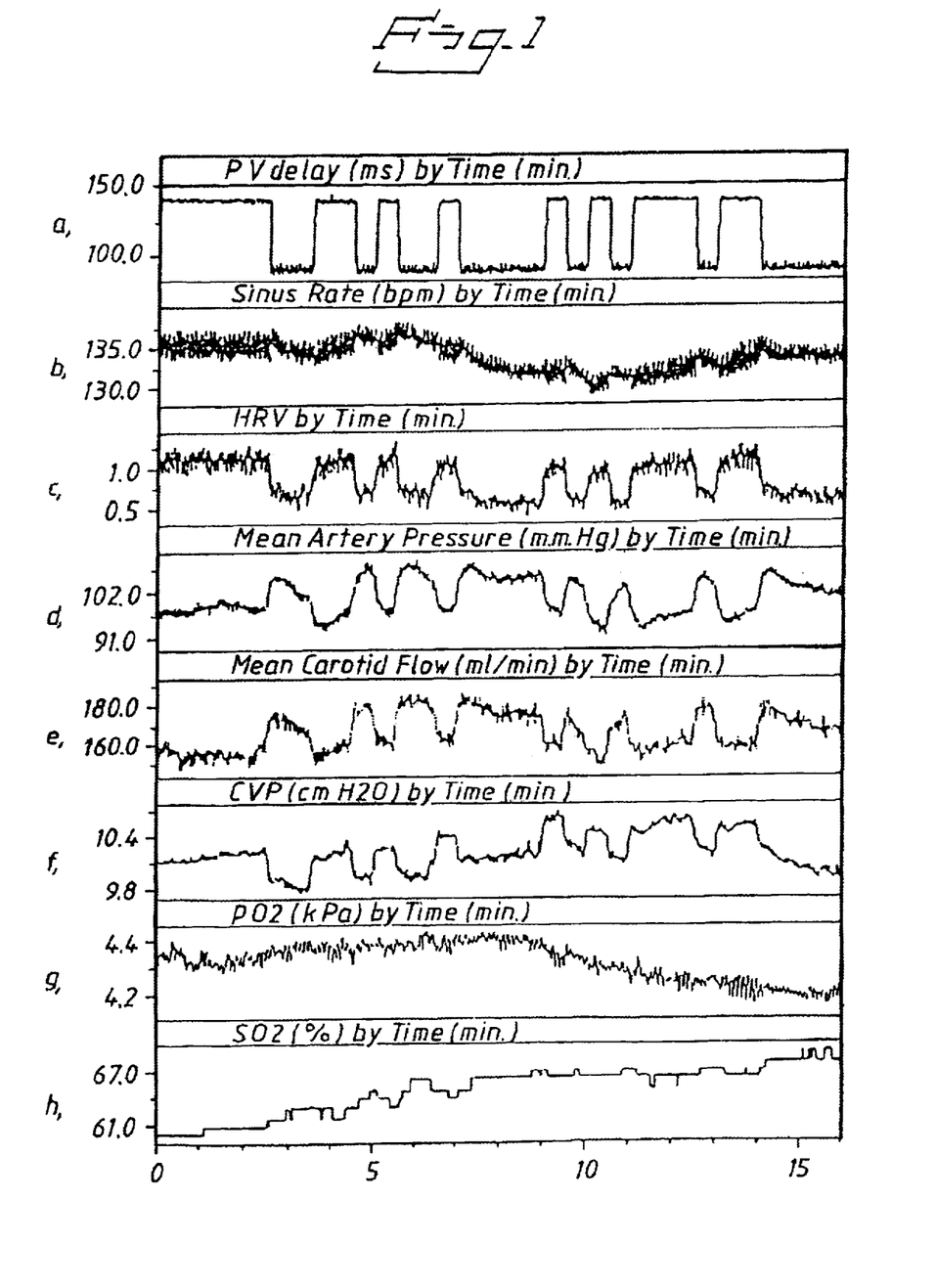
FIG. 1 shows experimental data obtained from animal studies, for explaining the present invention.

FIG. 1 shows experimental data obtained from an animal study and illustrates the dependence of several cardiac performance parameters on the AV delay (or PV delay). The AV delay was altered between 80 and 130 msec, see curve a. 15 changes were performed during a period of 16 minutes while monitoring the sinus rate, curve b, the heart rate variability (HRV), curve c, the mean artery pressure, curve d, the mean carotid flow, curve e, the central venous pressure (CVP), curve f, the right atrial oxygen pressure (pO2), curve g, and oxygen saturation (SO2), curve h. A very pronounced correlation between the AV-delay, curve a, and some of the measured parameters like heart rate variability (HRV), curve c, mean artery pressure, curved, mean carotid flow, curve e, and central venous pressure (CVP), curve f, is noticed. Corresponding variations in the oxygen pressure (pO2), curve g, and oxygen saturation (SO2), curve h, are less pronounced.

SUMMARY OF THE INVENTION

An object of the present invention is to improve the ability to determine the dependence of different cardiac performance parameters on the AV delay in a cardiac pacemaker, such that significant information can also be extracted from parameters such as the oxygen pressure (pO2) and oxygen saturation (SO2).

The above object is achieved in accordance with the invention in a pacemaker having a pulse generator for delivering stimulation pulses to a patient's heart, a control unit for controlling the delivery of the stimulation pulses from the pulse generator, an altering unit in the control unit for altering the AV delay from a predetermined first AV delay value to a predetermined second delay value, and back to the first AV delay value, and a sensor for measuring a parameter relating to cardiac output of the patient, wherein the sensor measures this parameter in a time window within a time of operation with the first AV delay value, as well as in a time window within a time of operation with said second AV delay value, and in a time window within a time of operation after the return back to the first AV delay value, and further having a determining unit including a calculation unit for calculating an average value of the parameter during each of the time windows, the determining unit using this average value to determine which of the AV delay values results in a higher cardiac output.

With a pacemaker according to the invention the atrial or ventricular pO2 or SO2 can be used for determining the dependency of cardiac output on the AV-delay. This is an important advantage since the pO2 sensor has proven to be especially suitable to use for this kind of measurements. The technique according to the invention can of course also be applied to other measured parameters, cf. FIG. 1, in order to get more distinct results, in particular if the measurement signals are affected by disturbances.

In an embodiment of the pacemaker according to the invention the calculation unit is adapted to form a first difference between average values obtained during the window positioned inside the time of operation with the first AV-delay value and obtained during the lime window within the time of operation with the second AV-delay value, as well as a second difference between average values obtained during the lime window within the time of operation with the second AV-delay value and the time window within the time of operation after the return of the AV-delay back to the first AV-delay value. These first and second differences are used in determining which AV-delay results in a higher cardiac output. In this way the possibility of extracting reliable information from the measurement signals is still more improved.

In a further embodiment of the pacemaker according to the invention in which the altering unit is adapted to repeatedly alter the AV-delay a number of times between the predetermined first and second AV-delay values, the calculation unit is adapted to form a mean value of a resulting number of the first differences and a mean value of a number of the second differences. These mean values are used in determining which AV-delay value results in a higher cardiac output. The possibility of the extracting information from the measurement signals is then further improved.

In another embodiment of the pacemaker according to the invention the altering unit is adapted, after determination of which one of said first and second AV-delay values indicates a higher cardiac output, to alter the AV-delay between this better AV-delay value and a third AV-delay value, and the determining unit is adapted to then determine which one of the better AV-delay value and the third AV-delay value results in an indication of a higher cardiac output. The altering unit repeats this procedure until an AV-delay value is determined which results in an indication of a highest cardiac output. Thus the pacemaker according to the invention will automatically find out the optimum AV-delay value and will then toggle around this optimum value. If conditions should change such that another AV-delay value is needed to obtain a maximum cardiac output, the pacemaker will automatically find this new optimum AV-delay value.

In another embodiment of the pacemaker according to the invention the altering unit alters the AV-delay values after times of operation according to a pseudo-stochastic sequence. Since several biological variations and external disturbances have cyclic characters, which can interfere with the measurements, it is an advantage not to use a cyclic variation of the AV-delays but instead to employ pseudo-stochastic sequences of delay values.

In another embodiment of the pacemaker according to the invention the time windows are positioned immediately before and immediately after an alteration of the AV-delay value. In this way changes in the measured parameter just related to the change of the AV-delay is determined and errors originating from variations in oxygen consumption's of the patient and sensor drift are minimized.

In further embodiments of the pacemaker according to the invention the sensor measuring a parameter related to cardiac output is one of the following types of sensors: a pO2-sensor, a SO2-sensor, a mean blood pressure sensor, a coronary artery flow sensor or a sinus rate sensor. If used, the blood pressure sensor is preferably adapted to measure the blood pressure in the vena cava or the right atrium. Artery blood pressure, mean blood pressure, systolic and diastolic pressure all correlate to cardiac output. As appears from FIG. 1 curve f the central venous pressure (CVP) responds very quickly and very distinctly to changes in the AV-delay. There is no delay in the CVP-response due to e.g. a blood circulation time as in the SO2-response, and the determination of best AV-delay value can in principle be performed even on a beat-to-beat basis. By applying a pseudo-stochastic sequence the desired result can be obtained by direct measurements on the CVP-response. However, by applying the technique according to the present invention on the signal from a CVP sensor the reliability of the obtained result is increased. Also, the mean carotid flow responds quickly and distinctly to changes of the AV-delay in an analogous way, cf. curve e in FIG. 1.

DESCRIPTION OF THE PREFERRED EMBODIMENTS

FIG. 1 illustrates experimental data obtained from studies on animal as explained above.

Figure 2:
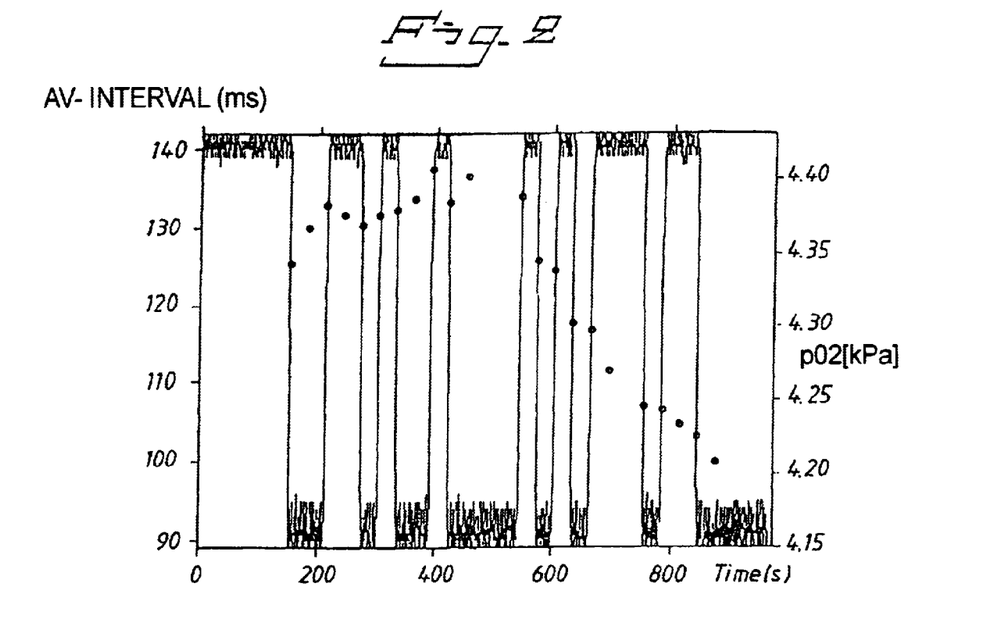
FIG. 2 shows the average pO2 at AV-delay change points.

FIG. 2 shows the AV-delay as a function of time according to curve a in FIG. 1 in an enlarged scale. In this example the upper AV-delay value is 130 msec and the lower value 80 msec. The AV-delay was altered according to a 32 bit pseudo-stochastic sequence. In this diagram dots are shown representing the average value of the measured pO2 during a period of 30 sec immediately before and immediately after each change in the AV-delay. The marked values are average values during 30 sec immediately preceding the position of the dot. The difference between each couple of average values from either side of the 15 transitions between the two AV-delay values shown in FIGS. 1 and 2 are given in table 1.

In table 1 the column "Step" indicates the number of the transition between the AV-delay values, counted from the left in FIG. 2. "Bits" indicates the bit number in the sequence, the column "AV STEP" indicates the direction of the transition. "neg" indicates a transition from 130 msec to 80 msec and "pos" a transition in the opposite direction. Column pO2-a indicates the average value during 30 msec immediately before the transition and pO2-b the average value during 30 msec immediately after the transition. The column pO2-duff indicates the difference between these two average values.

Figure 3:
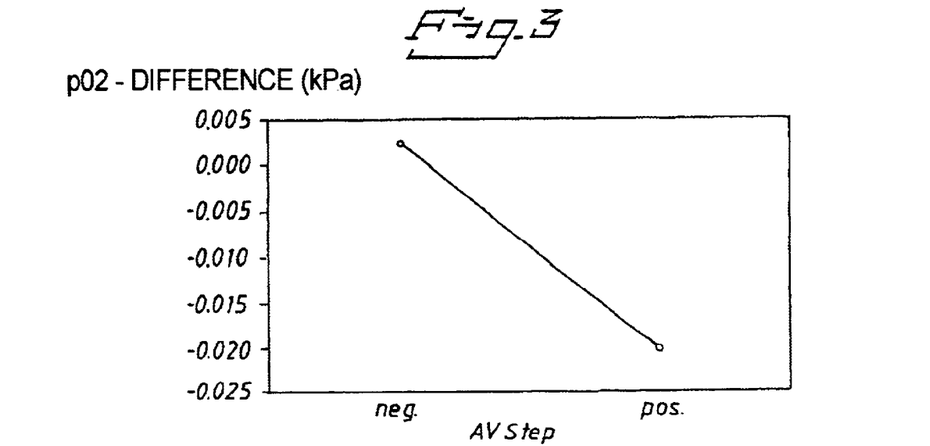
FIG. 3 illustrates the result obtained by analysis of the data in FIG. 2 by the pacemaker according to the invention.

FIG. 3 shows the average value of pO2-diff for negative transitions, to the left in FIG. 3, and for positive transitions, to the right in FIG. 3. From FIG. 3 it appears that a negative AV-transition—from 130 to 80 msec—increased the pO2-difference with 0.003 kPa, whereas a positive AV-step from 80 to 130 msec decreased the pO2-difference with 0.020 kPa. This significant difference between the two pO2-differences indicates that the shorter AV-delay of 80 msec is more effective than the longer delay.

Figure 8:
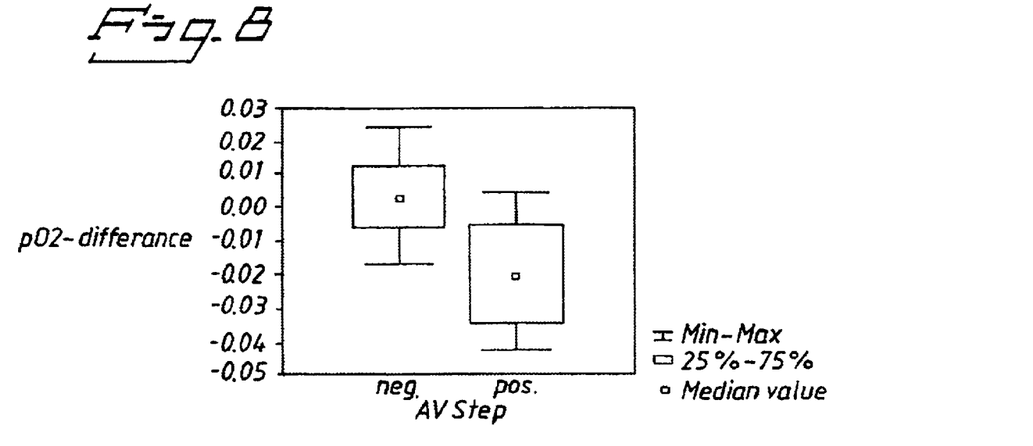
FIG. 8 illustrates the spread and medium value of pO2 differences obtained from the data shown in FIG. 2 and presented in Table 1.

In FIG. 8 the minimum and maximum values of the used pO2 differences are shown as well as the 25%–75% spread of these values and for the median values. These results are obtained by an analysis of variance of the measured data, cf. below.

The animal studies described above show that it is possible to statistically distinguish an optimum and a suboptimum AV-timing. It is possible to identify hemodynamic improvements of cardiac output by measuring changes in O2 after a step change of the AV-delay. The oxygen contents can be measured electro-chemically, by a pO2-sensor, or optically by a SO2 sensor.

Thus in the example described above the AV-delay, or the timing of the pulse generator of the pacemaker, is altered between two settings, e.g. a level A and a level B, one of which is the "better" one. By forming the difference between the average oxygen content, Δp (AB) during a time window of predetermined length immediately before a change of the AV-delay and during a time window of the same length immediately after the change from level A to level B, and comparing this result with the corresponding difference, Δp (BA), when the AV-delay is changed in the opposite direction from level B to level A, it is possible to find the best setting, A or B. The length of the time window is suitably in the range of 15–120 sec and the sampling interval within the range of 2–10 sec. The described procedure can be repeated and the results averaged for obtain a better resolution as described above.

If $\Delta p(AB) < \Delta p(BA)$ setting A of the AV-delay gives a higher O2 content indicating a better ventricular performance.

If $\Delta p(AB) > \Delta p(BA)$ setting B of the AV-delay give a better cardiac performance.

Figure 4:
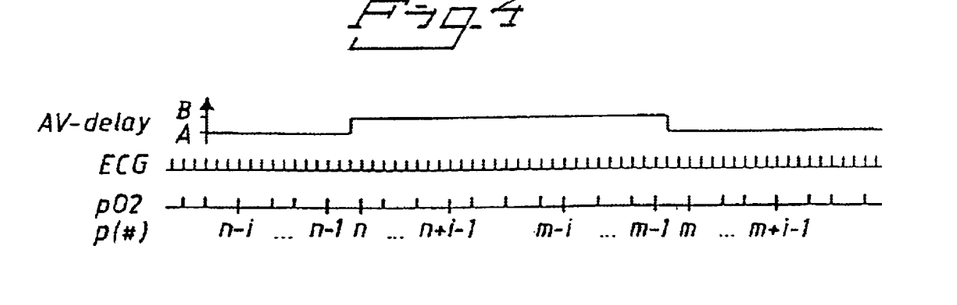
FIG. 4 illustrates the differential technique implemented in the pacemaker according to the invention to obtain an optimum AV delay.

In FIG. 4 n is defined as the first oxygen measurement p(n) after a step change of the AV-delay from level A to level B. The sample # m is defined as the first oxygen measurement p(m) after a change of AV-delay from level B to level A. The number of averaged O2 samples is denoted by i, in FIG. 4, i=4.

FIG. 4 illustrates the differential technique according to the invention for selecting the best AV-delay value as explained above.

After # n+i-1 measurements of O2 it is possible to calculate the O2 response of a change of the AV-delay from level A to level B according to the equation.

$$\Delta p(AB) = \frac{1}{i}\left(\sum_{x=1}^{i} p(n-x) - \sum_{x=1}^{i} n+x-1\right)$$

After # m+i-1 O2 measurements it is possible to calculate the O2 response of a change of the AV-delay from level B to level A according to equation.

By repeating this procedure several times u the risk of fault decisions is $$\Delta p(BA) = \frac{1}{i}\left(\sum_{x=1}^{i} p(m-x) - \sum_{x=1}^{i} m+x-1\right)$$

practically eliminated. The corresponding mean values $\Psi(A, B)$ are given by the following equations $$\Psi(AB) = \frac{1}{u}\sum_{x=1}^{u} \Delta p(AB)(x)$$

$$\Psi(BA) = \frac{1}{u}\sum_{x=1}^{u} \Delta p(BA)(x)$$

Thus if $\Psi(AB)\Psi<(BA)$ the AV-delay value B does not improve the heart performance compared to the situation with an AV-delay value equal to level A.

Figure 5:
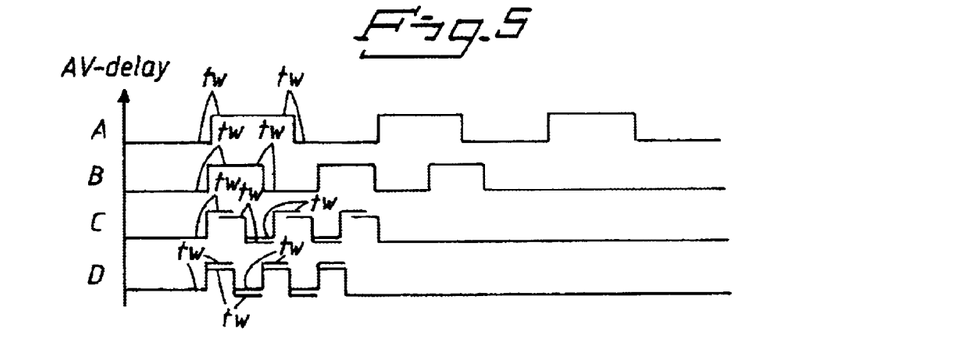
FIG. 5 illustrates different types of sampling measured parameter values.

Different types of differentiation of the O2 signal can be used. In the example above and in situations "A" and "B" in FIG. 5 the time windows, in which the measurements are performed, i.e. the measurements samples are taken, do not overlap. In the type of differentiation illustrated at "C" and "D" in FIG. 5 the same measurement samples are sometimes used twice, since adjacent time windows, in which the measurements are carried out, overlap. The time windows in question are marked tw. Curve A illustrates a situation with an intermediate time interval between each couple of time windows in which measurements are performed, curve B illustrates a situation in which consecutive measurement time windows directly follow each other, curve C illustrates a situation with partially overlapping measurement time windows and curve D illustrates a situation in which the time windows are totally overlapping.

Figure 6:
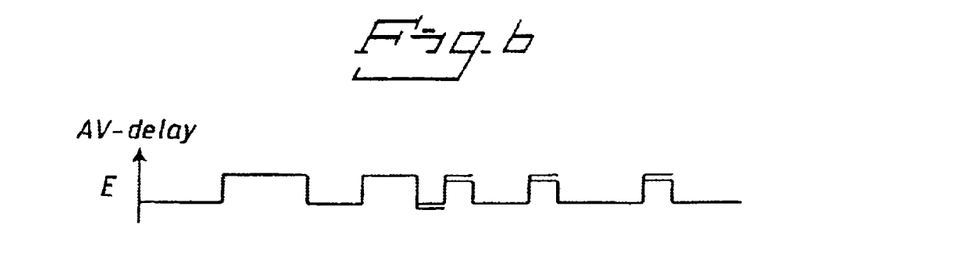
FIG. 6 shows a psuedo-stochastic AV-delay sequence.

It is an advantage not to use a cyclic variation of the AV-delay, since many biological variations and external disturbances are cyclic which consequently can interfere with the measurements. It may therefore be an advantage to change the AV-delay according to a pseudo-stochastic sequence as illustrated in FIG. 6.

Figure 7:
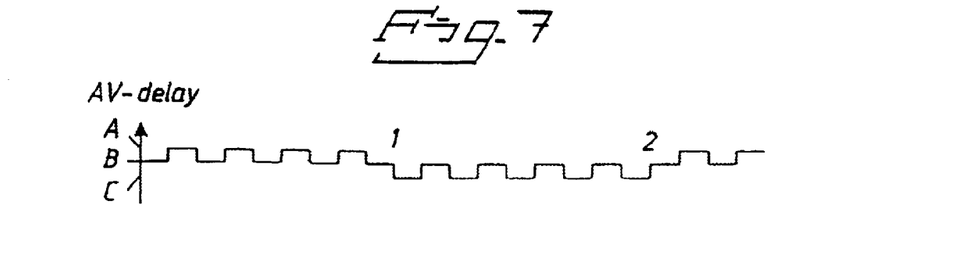
FIG. 7 shows the AV-delay sequence when an optimum AV-delay is reached.

When an AV-delay value has been selected as the "better" one, this "better" value is used in a new comparison procedure in which it is compared with another AV-delay. In each step of this selection procedure the AV-delay value is favored which results in the highest O2 value, and when the optimum AV-delay value is reached, the AV-delays will toggle around this optimum value, as illustrated in FIG. 7. In the shown example an AV-delay equal to B is supposed to give a better O2 value than an AV-delay equal to A. Further, an AV-time equal to B is also supposed to give a better O2 value than an AV-time equal to C.

From the description above it appears that, if the situation of the patient changes such that the optimum AV-delay is changed, the pacemaker according to the invention will automatically found out a new optimum value and the pacemaker will operate with this new AV-delay.

Figure 9:
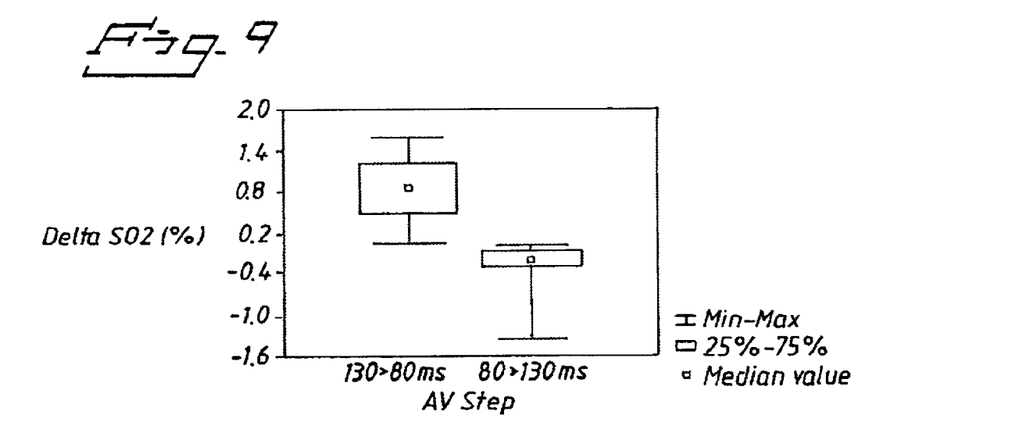
FIGS. 9–13 are respective diagrams for the parameters oxygen saturation (SO2), central venous pressure (CVP), mean blood pressure (MBP), carotid artery flow (CAF), and sinus rate (SR).
Figure 10:
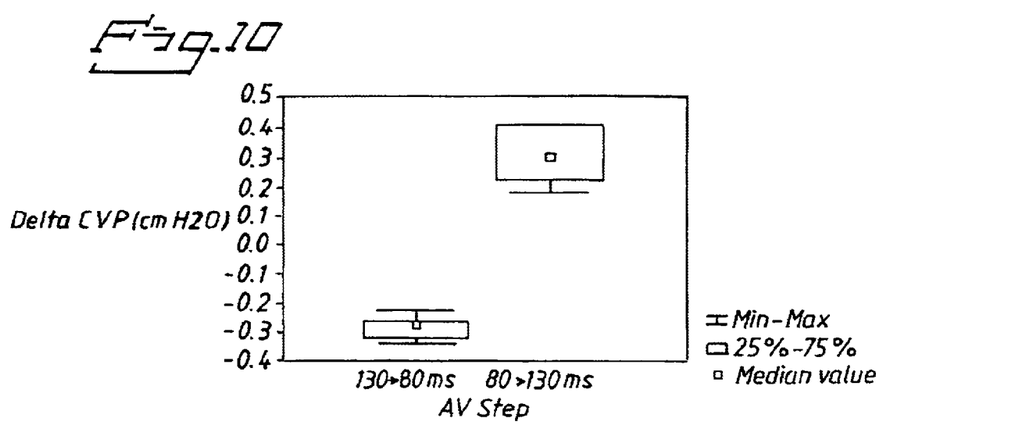
Figure 11:
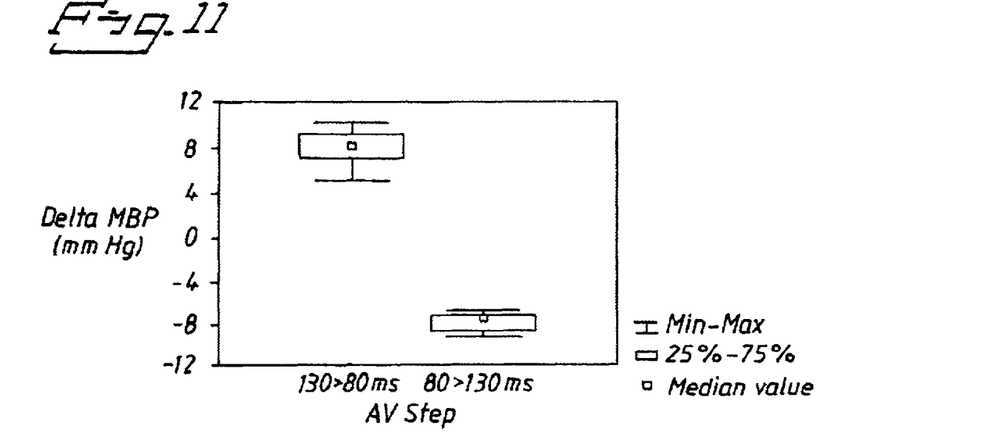
Figure 12:
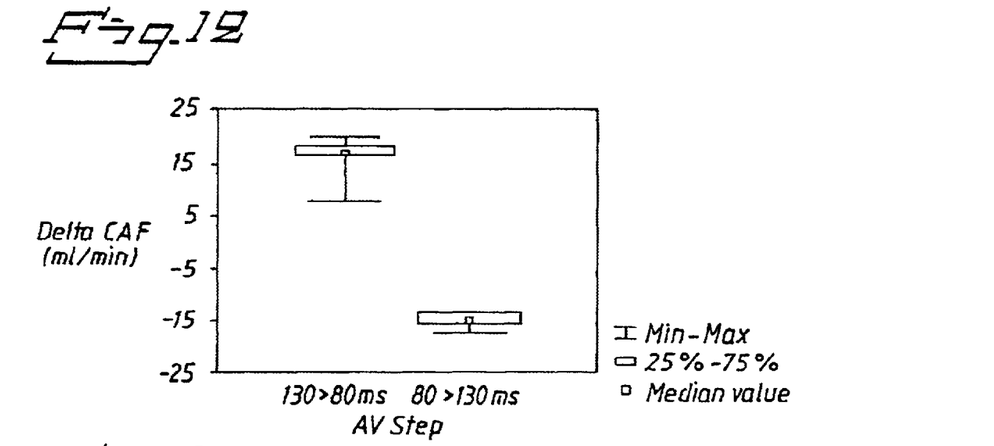
Figure 13:
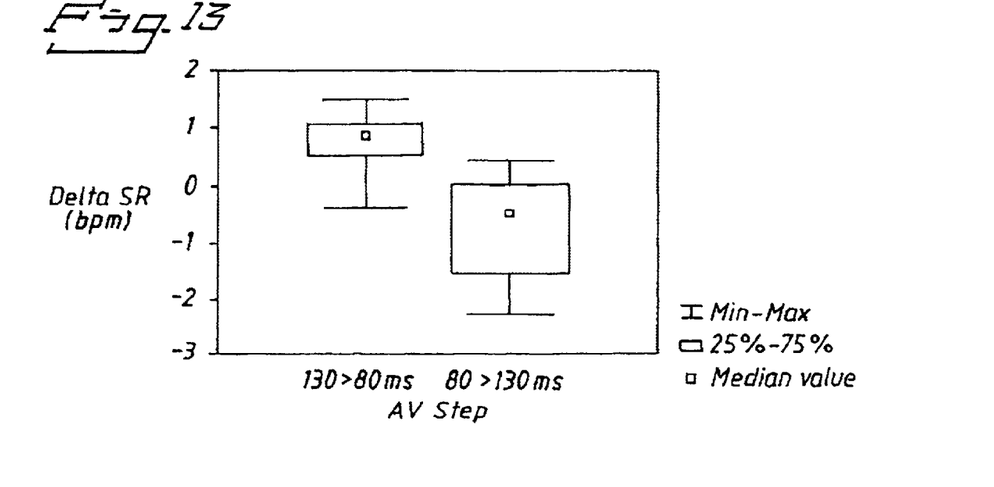

FIGS. 9–13 are diagrams corresponding to FIG. 8 showing the limits for minimum and maximum values, the 25%–75% spread and the median values of the parameters obtained at animal studies described in connection with FIG. 1. Thus FIG. 9 shows these values for the SO2 difference, FIG. 10 the results for the central venous pressure differences Delta CVP, FIG. 11 the mean blood pressure difference, Delta MBP, FIG. 12 the carotid artery flow difference, Delta CAF, and FIG. 13 the sinus rate difference, Delta SR.

The analysis of all these parameters clearly shows that an AV-delay value of 80 msec is better than an AV-delay value of 130 msec.

The differential technique described above is a simple way of eliminating errors originating from variations in oxygen consumption of the patient and sensor drift. It is also advantages to use this technique because the variations of the oxygen content due to AV-delay changes are much smaller that changes in the oxygen content due to metabolic variations and also other factors.

Figure 14:
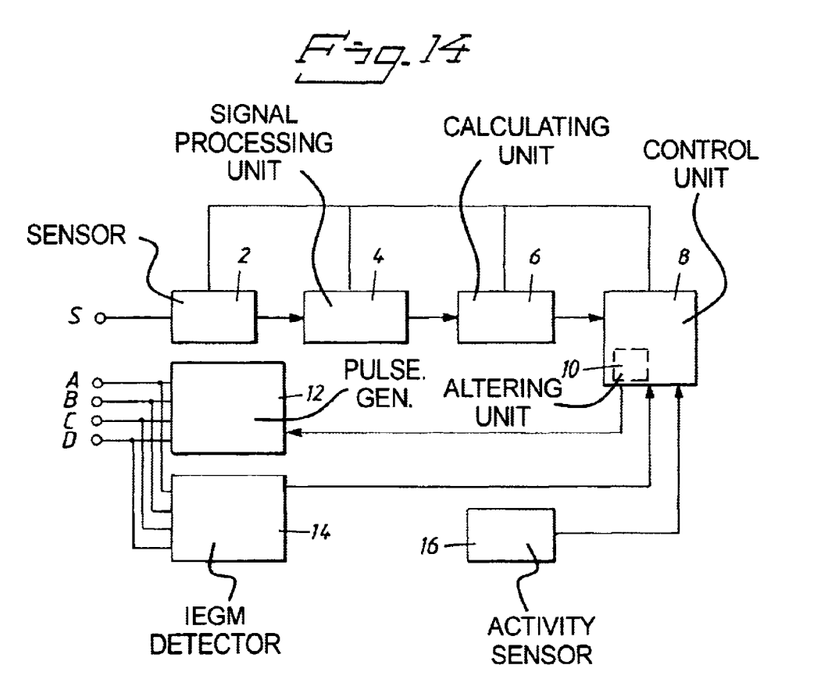
FIG. 14 is a block diagram of a closed loop regulation system of the pacemaker according to the invention.

FIG. 14 shows a block diagram of the basic layout of the pacemaker according to the invention. The pacemaker has a sensor 2, preferably a pO2-sensor, for measuring a parameter related to cardiac output of the patient (=e.g. oxygen pressure). The measurement signals are processed in a suitable signal processing unit 4 and the average value during predetermined time windows immediately before and after a change in the AV-delay is calculated in the calculating means 6. In this calculating means 6 the difference between average values obtained in the respective time window on each side of an AV-delay transition are calculated, and finally a mean value is determined for this difference for "negative" transitions and "positive" transitions in the AV-delay, respectively, as described above, for determining which one of the AV-delay values results in a higher cardiac output. This result is supplied to a control unit 8 including an altering unit 10.

The timing of the pulse generator 12 is then controlled by the altering unit 10 to change the AV-delay between this "better" AV-delay value and a new AV-delay value, In the example above a change of the AV-delay between 130 msec and 80 msec is described. In practice the difference between the two AV-delay values can suitably be 20 msec.

The length of the time window in which the measurements are performed can also be varied and the sampling frequency can also be varied from the control unit 8.

An IEGM detector 14 is also connected to the controlling means 8, a.o. to synchronize the measurements to the cardiac cycle of the patient.

The optimum AV-delay at rest is longer than at exercise. Different activity levels therefore have to be distinguished. Considerable variations in activity level can, however, give rise to problems. The easiest way to avoid such problem is to inhibit the AV-selection function of the pacemaker when an activity sensor indicates exertion by the patient exceeding a predetermined threshold level. An activity sensor 16 is therefore connected to the control unit 8. This activity sensor can be the O2 sensor used and/or e.g. a movement sensor. If an increased activity persists over a longer time it is possible with the pacemaker according to the invention to search a new optimum AV-delay at this defined level of workload. In such a state it is probably advantageous to have a shorter decision time for deciding the optimum AV-delay than at rest condition.

The sensor used in the pacemaker according to the invention is preferably an electrochemically pO2-sensor of the kind described in WO 98/14772. The invention is, however, not limited to the use of such a sensor. A pO2-sensor can be implanted together with an implanted pacemaker, e.g. for measuring the oxygen concentration in the right atrium. However, variations of the oxygen content in e.g. the ventricle or arteria pulmonaris can be continuously measured in a corresponding way. Further, with a pO2-sensor the measuring pulses can be made so short that synchronization of the measurement to the cardiac cycle is possible, and the pO2-sensor has proved to give reliable measurement results over time.

The invention has been explained above primarily in connection with the optimization of the AV-delay in dual chamber pacemakers. However, as mentioned before the PV-interval between the occurrence of an intrinsic P-wave and the application of a cardiac stimulation pulse can be different from the AV-interval between consecutive cardiac stimulation pulses to the atrium and the ventricle respectively. Therefore these intervals ought to be optimized separately if a patient utilizes both intervals. Further, in pacemakers designed for biatrial and biventricular stimulation it is not always optimum to stimulate left and right ventricle simultaneously. The time interval between left and right stimulation should therefore preferably be optimized. A proper delay will result in hemodynamic advantages, reflected in an increased cardiac output. The described technique can also be used in such pacemakers for multi-site stimulation for simultaneously optimizing several time intervals or delays, like these mentioned time intervals. In this way patients having e.g. a bundle block or a prolonged interatrial conduction time can be aided as well.

Although modifications and changes may be suggested by those skilled in the art, it is the invention of the inventors to embody within the patent warranted heron all changes and modifications as reasonably and properly come within the scope of their contribution to the art.

We claim:

1. A cardiac pacemaker comprising:
   a pulse generator which emits stimulation pulses adapted for delivery to a heart in a patient;
   a control unit connected to said pulse generator for controlling emission of said stimulation pulses by said pulse generator;
   an altering unit in said control unit for altering an AV-delay associated with said stimulation pulses from a predetermined first AV-delay value to a predetermined second AV-delay value, and back to said first AV-delay value;
   a sensor adapted to interact with said patient to measure a parameter related to cardiac output of said patient, said sensor measuring said parameter in a first time window within a time of operation with said first AV-delay value, and in a second time window within a time of operation with said second AV-delay value, and in a third time window within a time of operation after the return back to said first AV-delay value;
   a calculating unit which calculates respective average values of said parameter in said first, second and third time windows; and
   a determining unit supplied with said average values for determining which of said first and second AV-delay values results in a higher cardiac output, said determining unit being connected to said control unit and said control unit then controlling said pulse generator to operate with said AV-delay value that results in a higher cardiac output.

2. A cardiac pacemaker as claimed in claim 1 wherein said calculation unit calculates a first average value from said parameters measured in said first time window, and calculates a second average value from said parameters measured in said second time window, and calculates a third average value from said parameters measured in said third time window, and wherein said calculation unit forms a first difference between said first and second average values and a second difference between said second and third average values, and wherein said determining unit uses said first difference and said second difference to determine which of said first and second AV-delay values results in a higher cardiac output.

3. A cardiac pacemaker as claimed in claim 2 wherein said sensor measures said parameter in a single time window, as said second time window, during said time of operation with said second AV-delay value.

4. A cardiac pacemaker as claimed in claim 2 wherein said sensor measures said parameter in a plurality of sub-windows, in combination forming said second time window, during said time of operation with said second AV-delay value.

5. A cardiac pacemaker as claimed in claim 2 wherein said altering unit alters said AV-delay between said first and second AV-delay values and back to said first AV-delay value in a plurality of alterations, and wherein said calculation unit calculates said first difference and said second difference for each of said alterations, and thereby produces a plurality of first differences and a plurality of second differences, and wherein said determining unit uses said plurality of first differences and said plurality of second differences to determine which of said first and second AV-delay values results in a higher cardiac output.

6. A cardiac pacemaker as claimed in claim 1 wherein said AV-delay value that results in a higher cardiac output is a better AV-delay value, and wherein said altering unit, alter said determining unit determines said better AV-delay value, alters said AV-delay value between said better AV-delay value and a third AV-delay value and back to said better AV-delay value, and wherein said sensor measures said parameter in respective time windows within operation during each of said better AV-delay value and said third AV-delay value, and wherein said calculation unit calculates respective further average values for the parameters respectively measured in said time windows during operation with said better AV-delay value and said third AV-delay value, and wherein said determining unit uses said further average values to determine which of said better AV-delay value and said third AV-delay value results in a higher cardiac output.

7. A cardiac pacemaker as claimed in claim 1 wherein said altering unit alters said AV-delay value a plurality of times between a plurality of different AV-delay values, and wherein said sensor measures said parameter in a plurality of time windows respectively during operation with each of said plurality of AV-delay values, each of said plurality of time windows being shorter than the respective times of operation with said plurality of AV-delay values, and wherein said calculation unit calculates a plurality of averages respectively for said plurality of parameters measured in said plurality of time windows, and wherein said determining unit uses said plurality of averages to determine which of said plurality of AV-delay values results in a highest cardiac output.

8. A cardiac pacemaker as claimed in claim 1 wherein said times of operation are equal.

9. A cardiac pacemaker as claimed in claim 1 wherein said times of operation are different.

10. A cardiac pacemaker as claimed in claim 1 wherein said altering unit alters said AV-delay values after respective times of operation according to a psuedo-stochastic sequence.

11. A cardiac pacemaker as claimed in claim 1 wherein said times of operation have respective durations in range of minutes.

12. A cardiac pacemaker as claimed in claim 1 wherein said sensor selects said time windows immediately before and immediately after alteration of said AV-delay value.

13. A cardiac pacemaker as claimed in claim 1 wherein said time windows have a duration in a range between 0.5 and 1 minute.

14. A cardiac pacemaker as claimed in claim 1 wherein said sensor samples said parameter with a sampling interval in range between 2 and 10 seconds.

15. A cardiac pacemaker as claimed in claim 14 further comprising a synchronization unit which synchronizes sampling by said sensor to a cardiac cycle of said heart.

16. A cardiac pacemaker as claimed in claim 1 wherein said sensor is a sensor selected from the group consisting of $pO_2$ sensors, $SO_2$ sensors, mean blood pressure sensors, coronary artery flow sensors and sinus rate sensors.

17. A cardiac pacemaker as claimed in claim 1 wherein said sensor is a blood pressure sensor adapted to measure blood pressure in the vena cava.

18. A cardiac pacemaker as claimed in claim 1 wherein said sensor is a blood pressure sensor adapted to measure blood pressure in the right: atrium of said heart.

* * * * *